United States Patent [19]

D'Amico

[11] 4,222,938

[45] Sep. 16, 1980

[54] PREPARATION OF THIOLCARBAMATES

[75] Inventor: John J. D'Amico, Olivette, Mo.

[73] Assignee: Monsanto Company, St. Louis, Mo.

[21] Appl. No.: 947,135

[22] Filed: Sep. 29, 1978

[51] Int. Cl.² .................. C07D 205/00; C07D 203/06; C07C 155/02; C07D 207/04

[52] U.S. Cl. ........................ 260/239 A; 260/239 BF; 260/239 E; 260/326.4; 260/455 A; 546/237; 546/245

[58] Field of Search .......... 260/326.4, 239 BF, 455 A, 260/239 E, 239 A; 546/245, 237

[56] References Cited

U.S. PATENT DOCUMENTS

| | | | |
|---|---|---|---|
| 2,723,989 | 11/1955 | Harman | 260/455 A |
| 2,913,326 | 11/1959 | Tilles et al. | 260/455 A |
| 2,913,327 | 11/1959 | Tilles et al. | 71/2.7 |
| 2,941,880 | 6/1960 | D'Amico | 71/217 |
| 2,983,747 | 5/1961 | Campbell et al. | 260/455 |
| 2,992,091 | 7/1961 | Harman et al. | 71/2.6 |
| 3,144,475 | 8/1964 | Harman et al. | 260/455 |
| 3,167,571 | 1/1965 | D'Amico et al. | 260/455 |
| 3,175,897 | 3/1965 | Tilles et al. | 71/2.6 |
| 3,230,243 | 1/1966 | D'Amico | 260/455 |
| 3,330,643 | 7/1967 | Harman et al. | 71/100 |
| 3,330,821 | 7/1967 | Harman et al. | 260/239 |
| 3,330,822 | 7/1967 | D'Amico | 260/239 |
| 3,687,653 | 8/1972 | Bollinger et al. | 71/94 |
| 3,963,768 | 6/1976 | Millauer et al. | 260/455 A |
| 4,003,735 | 1/1977 | Czajkowski et al. | 71/101 |

FOREIGN PATENT DOCUMENTS 7036014  7/1971  France ................. 260/455 A

OTHER PUBLICATIONS

H. Tilles, JACS, 81, pp. 714–727, Thiolcarbamates, Preparation and molar refractions, (1958).

*Primary Examiner*—Donald G. Daus
*Assistant Examiner*—M. C. Eakin
*Attorney, Agent, or Firm*—Patricia A. Coburn; Donald W. Peterson

[57] ABSTRACT

Thiolcarbamates are prepared from carbamoyl halides and xanthates.

5 Claims, No Drawings

PREPARATION OF THIOLCARBAMATES

PREPARATION OF THIOLCARBAMATES

This invention relates to a process for preparing thiolcarbamates. More particularly, this invention relates to the preparation of thiolcarbamates by reaction of a carbamoyl halide with a xanthate.

Thiolcarbamates are known to be useful in controlling the growth of undesired vegetative growth. U.S. Pat. No. 2,913,327 as well as U.S. Pat. Nos. 2,992,091 and 3,175,897 disclose thiolcarbamates to be useful herbicides. Similarly, U.S. Pat. Nos. 2,941,880; 3,230,243; 3,330,822; and 3,687,653 disclose the use of thiolcarbamates as herbicides. Recently, U.S. Pat. No. 4,003,735 disclosed that certain thiolcarbamates, especially those in which the nitrogen atom had a phenyl moiety attached thereto, were effective in safening crop plants against herbicidal injury due to acetanilide herbicides. Those patents disclose various methods for preparing thiolcarbamates, many of which have been summarized in an article by H. Tilles in *Journal of The American Chemical Society*, Volume 81, Page 714 (1958). In accordance with that article, thiolcarbamates have been prepared by reaction of a mercaptan or sodium mercaptide with a disubstituted carbamoyl chloride in refluxing xylene. As will be appreciated by those skilled in the art, mercaptans are highly toxic, odoriferous compounds that are easily oxidizable to the corresponding disulfide. Another process known for preparing thiolcarbamates is the condensation of an alkyl chlorothiolformate with a secondary amine. Alkyl chlorothiolformates, however, are toxic, odoriferous, lachrymators and have poor storage stability. Thiolcarbamates are also prepared by reacting a secondary amine with carbonyl sulfide, an alkyl halide and a base. This reaction, however, must be carried out at rather low temperatures and utilizes excess amine which must later be recovered. Even though, therefore, there are numerous methods for preparing thiolcarbamates, each suffers from various drawbacks.

An object of the present invention, then, is to provide a process for preparing thiolcarbamates that is fast, economical, efficient and uncomplicated by side reactions.

A second object is to provide a process for preparing thiolcarbamates that does not require the use of either mercaptans or alkyl chlorothiolformates.

Still another object of the invention is to provide a process that eliminates the necessity for complex chemical separations in order to purify the desired thiolcarbamate.

These and other objects of the invention are accomplished by preparing a thiolcarbamate by reaction of a carbamoyl halide and a xanthate. For purposes of clarity, the following chemical equation is presented to illustrate the simplicity of the novel process:

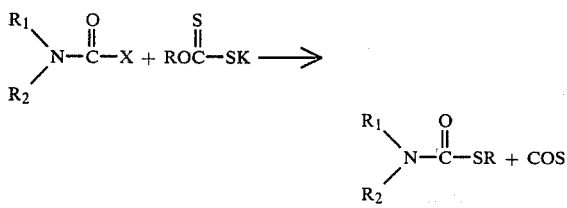

In the above process, X represents a halogen, preferably chlorine. As can be appreciated by those skilled in the art, R, $R_1$ and $R_2$ do not appreciably take part in the reaction. Accordingly, the nature of these groups is not critical. Thus, $R_1$ and $R_2$ can independently be a monovalent organic radical or when taken together with the nitrogen atom form a heterocycle. R represents a radical selected from the group consisting of alkyl, substituted or unsubstituted alkenyl and substituted or unsubstituted benzyl. Conveniently, $R_1$ and $R_2$ may independently be alkyl, alkenyl, phenyl, substituted phenyl, benzyl or substituted benzyl. When taken together with the nitrogen atom, $R_1$ and $R_2$ may form a heterocycle, such as ethyleneimine, trimethyleneimine, pyrrolidine, piperidine, hexamethyleneimine and the like.

By the term "substituted alkenyl" is meant those alkenyl moieties in which a hydrogen has been replaced by one or more halogen moieties. The term "substituted phenyl" or "substituted benzyl" referes to those phenyl and benzyl moieties having one or more radicals on the ring selected from the group consisting of alkyl having up to five carbon atoms, inclusive, halogen, nitro, trifluoromethyl and the like substituted on the phenyl ring.

R may conveniently be methyl, ethyl, n-propyl, isopropyl, n-butyl, sec-butyl, t-butyl and the like (especially those alkyl groups having up to five carbon atoms, inclusive), allyl, monochloroallyl, dichloroallyl, trichloroallyl, benzyl in which the phenyl ring of said benzyl moiety may optionally be substituted with one or more moieties independently selected from the group consisting of alkyl having up to five carbon atoms, inclusive, halogen, nitro, CF3 and the like.

The formation of thiolcarbamates by the process described above is quite unexpected. One skilled in the art would expect the formation of an anhydride in accordance with the following equation:

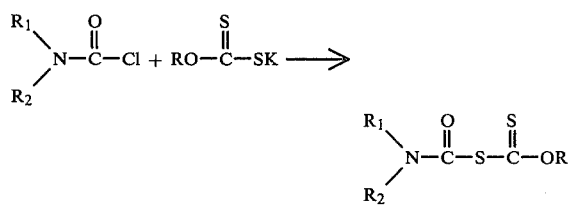

Said anhydride does not form, or if it does, it decomposes immediately to give carbonyl sulfide and the thiolcarbamates.

Typically, inert solvents are utilized to facilitate the reaction between the carbamoyl halide and the xanthate. Examples of such solvents include, but are not limited to, acetone, benzene, chloroform, methylene chloride, toluene and tetrahydrofuran.

In order to further illustrate the process of the invention, the following examples are presented and are not intended as a limitation with respect to the scope thereof.

EXAMPLE 1

To a stirred slurry containing 0.33 moles of potassium benzyl dithiocarbonate dihydrate in 200 ml. of acetone, 0.3 moles of diethylcarbamoyl chloride is added. The stirred reaction mixture was heated at reflux for 6 hours and then at 25°-30° C. for 18 hours. During heating, carbonyl sulfide was liberated. To the stirred reaction mixture, 600 ml. of water and 600 ml. of ethyl ether were added and stirring continued at 25°-30° C. for 15 minutes. The separated ether layer was washed with water until neutral to litmus and dried over sodium sulfate. The ether was removed in vacuo at a maximum temperature of 80° C. at 1-2 mm. The data is summarized in Table I, below.

EXAMPLE 2

The procedure of Example 1 is repeated utilizing potassium ethyl dithiocarbonate dihydrate in lieu of potassium benzyl dithiocarbonate dihydrate and 1-pyrrolidinecarbamoyl chloride in lieu of diethylcarbamoyl chloride. Data is summarized in Table I, below.

EXAMPLE 3

The procedure of Example 2 is repeated utilizing dimethylcarbamoyl chloride in lieu of 1-pyrrolidinecarbamoyl chloride. Data is summarized in Table I, below.

EXAMPLE 4

The procedure of Example 1 is repeated utilizing potassium methyl dithiocarbonate dihydrate in lieu of potassium benzyl dithiocarbonate and N-methyl-N-phenylcarbamoyl chloride in lieu of diethylcarbamoyl chloride. Data is summarized in Table I, below.

EXAMPLE 5

The procedure of Example 2 is repeated utilizing N-cyclohexyl-N-(2-chloroallyl) carbamoyl chloride in lieu of 1-pyrrolidinecarbamoyl chloride. Data is summarized in Table I, below.

EXAMPLE 6

The procedure of Example 1 is repeated utilizing N-cyclohexyl-N-(2-chloroallyl) carbamoyl chloride in lieu of diethylcarbamoyl chloride. Data is summarized in Table I, below.

Although the reaction proceeds where a stoichiometric equivalent of carbamoyl halide and xanthate is utilized, a slight excess of xanthate is preferred.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for the preparation of thiolcarbamates having the formula:

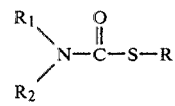

wherein $R_1$ and $R_2$ are independently equal to alkyl, alkenyl, phenyl, benzyl or phenyl or benzyl substituted on the ring by one or more radicals selected from the group consisting of alkyl having up to five carbon atoms, halogen, nitro and trifluoromethyl or $R_1$ and $R_2$ when taken together with the nitrogen atom are equal to ethyleneimine, trimethyleneimine, pyrrolidine, piperidine or hexamethyleneimine; R is equal to alkyl, alkenyl, alkenyl substituted by one or more halogen moieties, benzyl or benzyl substituted by one or more moieties independently selected from the group consisting of alkyl having up to 5 carbon atoms, halogen, nitro and trifluoromethyl, which comprises reacting a carbamoyl halide having the formula

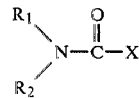

Table I $$\underset{R_2}{\overset{R_1}{\diagdown}}N-\overset{\overset{O}{\|}}{C}-X + RO\overset{\overset{S}{\|}}{C}-SK \longrightarrow \underset{R_2}{\overset{R_1}{\diagdown}}N-\overset{\overset{O}{\|}}{C}-SR + COS$$

| Compound of Example No. | $R_1$ | $R_2$ | R | M.P. °C. (B.P. °C./mm) | % Yield | | % C | % H | % N | % S |
|---|---|---|---|---|---|---|---|---|---|---|
| 1 | —$C_2H_5$ | —$C_2H_5$ | —$CH_2C_6H_5$ | (132–3/1 mm) | 67 | Calc'd: | 64.54 | 7.67 | 6.27 | 14.36 |
|   |   |   |   |   |   | Found: | 64.36 | 7.76 | 6.00 | 14.06 |
| 2 | ⌐N—⌐ |   | —$C_2H_5$ | (92–3/1 mm) | 63 | Calc'd: | 52.80 | 8.23 | 3.80 | 20.13 |
|   |   |   |   |   |   | Found: | 52.78 | 8.23 | 8.79 | 20.06 |
| 3 | —$CH_3$ | —$CH_3$ | —$C_2H_5$ | (30–1/0.3 mm) | 85 | Calc'd: | 45.08 | 8.32 | 10.51 | 24.07 |
|   |   |   |   |   |   | Found: | 44.89 | 8.18 | 10.47 | 23.93 |
| 4 | —$C_6H_5$ | —$CH_3$ | —$CH_3$ | 47–8 | 91 | Calc'd: | 59.64 | 6.12 | 7.73 | 17.69 |
|   |   |   |   |   |   | Found: | 59.71 | 6.19 | 7.73 | 17.57 |
| 5 | —$C_6H_{11}$ | —$CH_2\overset{Cl}{\underset{|}{C}}=CH_2$ | —$C_2H_5$ | (140–2/1 mm) | 50 | Calc'd: | 55.05 | 7.70 | 5.35 | 12.25 |
|   |   |   |   |   |   | Found | 55.20 | 7.73 | 5.34 | 12.22 |
| 6 | —$C_6H_{11}$ | —$CH_2\overset{Cl}{\underset{|}{C}}=CH_2$ | —$CH_2C_6H_5$ | Stripped at max. temp. of 195 at 1–2 mm | 96 | Calc'd: | 63.04 | 6.85 | 4.32 | 9.90 |
|   |   |   |   |   |   | Found: | 63.23 | 6.89 | 4.30 | 9.91 |

As can be appreciated from the above examples, the process is preferably conducted at atmospheric pressure, although sub-atmospheric and super-atmospheric pressures may be employed. Preferably, the reaction is conducted by heating the reaction mixture to a temperature ranging from 25° C. to the reflux temperature of the mixture.

wherein X is a halogen and a xanthate having the formula

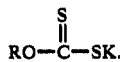

2. A process according to claim 1 wherein X is chlorine.

3. A process according to claim 1 wherein said reaction is conducted in an inert solvent.

4. A process according to claim 1 wherein $R_1$ and $R_2$ when taken together with the nitrogen atom are equal to ethyleneimine, trimethyleneimine, pyrrolidine, piperidine or hexamethyleneimine.

5. A process according to claim 1 wherein $R_1$ is equal to cyclohexyl.

* * * * *